United States Patent [19]

Kaplan et al.

[11] 4,153,623

[45] May 8, 1979

[54] PROMOTING PROPYLENE GLYCOL FORMATION WITH COMPOUNDS OF ALUMINUM

[75] Inventors: Leonard Kaplan, Charleston; Wellington E. Walker, Sissonville; George L. O'Connor, Charleston, all of W. Va.

[73] Assignee: Union Carbide Corporation, New York, N.Y.

[21] Appl. No.: 814,736

[22] Filed: Jul. 11, 1977

[51] Int. Cl.$^2$ .................... C07C 27/06; C07C 31/06
[52] U.S. Cl. ............................ 260/449 L; 252/431 R; 252/431 N; 260/449.5
[58] Field of Search ........................ 260/449 R, 449 L

[56] References Cited

U.S. PATENT DOCUMENTS 3,833,634  6/1974  Pruett et al. .................... 260/449 R Primary Examiner—Howard T. Mars
Attorney, Agent, or Firm—Bernard Lieberman

[57] ABSTRACT

This invention relates to the manufacture of such valuable chemicals as polyhydric alcohols, their ether and ester derivatives, oligomers of such alcohols and their ether and ester derivatives by reacting hydrogen and oxides of carbon in the presence of a rhodium carbonyl complex and a compound of aluminum.

5 Claims, No Drawings

PROMOTING PROPYLENE GLYCOL FORMATION WITH COMPOUNDS OF ALUMINUM

This invention relates to the production of polyhydric alcohols, their ether and ester derivatives, and oligomers of such alcohols. This invention also produces monohydric alcohols such as methanol and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making alkane diols and triols, containing 2, 3, or 4 carbon atoms, and derivatives such as their esters. Key products of the process of this invention are propylene glycol, ethylene glycol and their derivatives. Byproducts of this invention are the lesser valuable, but valuable nevertheless, monohydric alkanols such as methanol, ethanol and propanol, and their ether and ester derivatives. The products of the process of this invention contain carbon, hydrogen and oxygen.

There are described in U.S. Pat. No. 3,833,634, issued Sept. 3, 1975, and U.S. Pat. No. 3,957,857, issued May 18, 1976, processes for reacting hydrogen and oxides of carbon in the presence of rhodium carbonyl complex catalysts to produce polyhydric alcohols, such as, ethylene glycol, monohydric alcohols, such a methanol, and their ether and ester derivatives. U.S. Pat. No. 3,957,857 is concerned with a rhodium carbonyl complex which is a rhodium carbonyl cluster exhibiting a particular infrared spectrum. U.S. Pat. No. 3,952,039, issued Apr. 20, 1976, is directed to the use of salts containing alkali metal cations in the reaction mixture to improve the yields of the alkane diols and triols of the invention. The conditions, broadly speaking, employed in these processes involve reacting a mixture of an oxide of carbon and hydrogen with a catalytic amount of rhodium in complex combination with carbon monoxide, at a temperature of between about 100° C. to about 375° C. and a pressure of between about 500 psia to about 50,000 psia.

It has been found that compounds of aluminum in a homogeneous liquid phase reaction mixture containing a catalytic amount of rhodium carbonyl complex promote the production of propylene glycol from a reaction mixture of hydrogen and oxides of carbon. Ethylene glycol is also produced by such reaction as a commercially valuable co-product.

The compounds of aluminum suitable for use in the present invention include aluminum carboxylates, trialkyl and triaryl aluminum compounds, aluminum alkanedionates, aluminum alkoxides, aluminum aryloxides and alkanolamine aluminates.

The term "oxides of carbon" as used throughout the specification and claims is intended to mean carbon monoxide and mixtures of carbon monoxide and carbon dioxide either introduced as such or formed in the reaction.

The rhodium carbonyl complexes suitable for use in the present invention may be in the form of rhodium carbonyl clusters. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster." The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal," "edge-bridging," and/or "face-bridging." They may also contain hydrogen and carbon in forms other than carbonyl. The following are illustrative of what is believed to be the structure of two distinct rhodium carbonyl clusters and both are suitable for use in this invention.

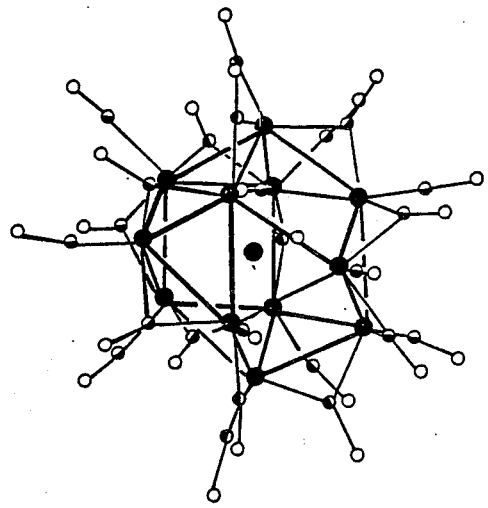

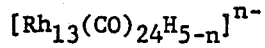

See V.A. Albano, et al, J.C.S. Chem. Comm., 859 (1975).

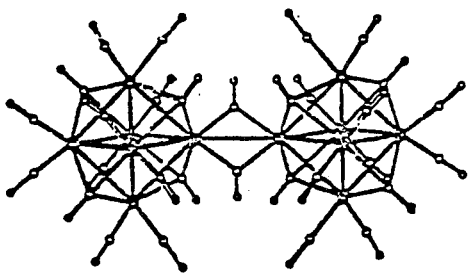

$[Rh_{12}(CO)_{30}]^{2-}$

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp 299-302, June (1969). Of particular analytical utility in the present invention is the use of infrared spectroscopy which allows for characterization of the particular rhodium carbonyl complex present during the operation of the process of the invention.

A particularly desirable infrared cell construction is described in U.S. Pat. No. 3,886,364, issued May 27, 1975 and its disclosure of a preferred cell construction is incorporated herein by reference.

The rhodium carbonyl complex is, as characterized above, a rhodium containing compound in which the rhodium is complexed with CO. This can be achieved with just carbon monoxide or in addition to the carbon monoxide there may be included hydrogen and/or other organic or inorganic Lewis base materials to create the complex. In the last case, "complex" means a coordination compound formed by the union of one or more electronically rich molecules or atoms capable of independent existence with one or more electronically poor molecules or atoms, each of which is also capable of independent existence. The precise role of these Lewis bases in the reaction of the present invention is not fully appreciated at present. They may be functioning as ligands and/or forming counter-ions under the reaction conditions of the present process or they may be functioning just merely as Lewis bases and neutralizing or tying up a molecular species which if allowed to remain "free" or in its non-base-bound state would adversely affect the productivity of the present invention.

Organic Lewis bases which are suitable in the practice of the present invention contain at least one Lewis base oxygen atom and/or one Lewis base nitrogen atom said atoms possessing a pair of electrons available for the formation of coordinate bonds. In suitable embodiments the organic Lewis bases contain from 1 and upwards to 4 Lewis base atoms, preferably from 1 to 3 such atoms, and most preferably 1 or 2 Lewis base atoms. These organic Lewis bases are said to be multidentate or polydentate, that is to say, they are bidentate, tridentate, or quadridentate, depending on whether 2, 3 or 4 Lewis base atoms are involved.

Those organic Lewis bases which contain at least one Lewis base nitrogen atom plus at least one Lewis base oxygen atom will oftentimes hereinafter be referred to as "organic aza-oxa" Lewis bases. Suitable nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N═), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

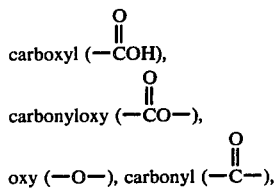

etc., all of said groups containing Lewis base oxygen atoms. In this respect, it is the "hydroxyl" oxygen in the

group and the "oxy" oxygen in the

group that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as ethanolamine, diethanolamine, isopropanolamine, di-n-propanolamine, and the like; N,N-dimethylglycine, N,N-diethylglycine;

iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like, morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amine are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention are promoters, as in the case of an amide, such as formamide, cyanamide, and urea, or an oxime. Further illustrative of these Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6,-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2'-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo[2.2.2]octane, purine and the like.

A normally liquid organic solvent is employed in an amount sufficient to maintain a homogeneous reaction mixture containing rhodium carbonyl cluster, the aluminum compound promoter and the reaction products.

Illustrative solvents which are generally suitable for the practice of the present invention include, for example, ethers such as tetrahydrofuran, tetrahydropyran, crown ethers [see, for example, Pedersen, J.A.C.S. vol. 89, No. 29, pp. 7017–7036 (Dec. 20, 1967)], diethyl ether, 1,2-dimethoxybenzene, 1,2-diethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethylenepropylene glycol, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water, gamma-butyrolactone, deltavalerolactone, substituted and unsubstituted tetrahydrothiophene-1,1-dioxides (sulfolanes) as disclosed in U.S. application Ser. No. 615,093, filed on Sept. 19, 1975, the disclosure at pages 6 and 7 of the specification being incorporated herein by reference; and others.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The novel process is suitably effected over a wide superatmospheric pressure range of from about 500 psia to about 50,000 psia. Pressures as high as 50,000 psia, and higher can be employed but with no apparent advantages attendant thereto which offset the unattractive plant investment outlay required for such high pressure equipment.

In one embodiment of this invention the upper pressure limitation is approximately 16,000 psia. Effecting the present process below about 16,000 psia, especially below about 13,000 psia, and preferably at pressures below about 8000 psia, results in cost advantages which are associated with low pressure equipment requirements. A suitable pressure range for effecting the reaction is from about 1000 psia to about 20,000 psia, preferably from about 4000 to about 16,000 psia.

In a preferred embodiment of the present invention the pressures referred to above represent the total pressures of hydrogen and oxides of carbon in the reactor.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Suitable operative temperatures are between about 150° C. to about 320° C., and desirably from about 210° C. to about 290° C.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or solvents, can be recycled to the reaction zone, if desired. All or a portion of such fraction can be removed for recovery of the rhodium values or regeneration to the active catalyst and can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium (II) propionate, rhodium(II) butyrate, rhodium(II) valerate, rhodium(III) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process.

The reaction of the present invention is conducted in what is believed to be a homogeneous liquid phase, which means that the catalyst, the aluminum compound promoter, the reaction products and other promoters which may be present are in solution. Though the reaction to produce alcohols is essentially homogeneous, there may be small amounts of insoluble catalyst particles depending on the reaction conditions employed.

In the examples below as set forth in the Table below, the following procedure was employed.

A 150 ml. capacity stainless steel reactor capable of withstanding pressures up to 7,000 atmospheres was charged with a premix of 75 cubic centimenters (cc) of a specified solvent, 3 millimoles (mmol) of rhodium in the form of rhodium dicarbonylacetylacetonate, and specified amounts of one or more of a compound of aluminum (where indicated), and salt promoter (where indicated). The reactor was sealed and charged with a gaseous mixture containing equal molar amounts of carbon monoxide and hydrogen to a pressure as specified below. Heat was applied to the reactor and its contents; when the temperature of the mixture inside the reactor reached 190° C., as measured by a suitably placed thermocouple, an additional adjustment of carbon monoxide and hydrogen ($H_2:CO=1:1$ mole ratio) was made to bring the pressure back to that which is specified in the Table. The temperatures and pressures were maintained as indicated in the Table.

After the reaction was terminated, the vessel and its contents were cooled to room temperature, the excess gas vented and the reaction product mixture was removed. Analysis of the reaction product mixture was made by gas chromatographic analysis using a Hewlett Packard FM TM model 810 Research Chromatograph.

The product weights (in grams) of propylene glycol, ethylene glycol and methanol as determined from the analysis of the product mixture is shown in the Table, as well as the rhodium recovery based on the total rhodium charged to the reactor.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for that experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values recited below are the percent rhodium based on the total rhodium charged to the reactor that is soluble or suspended in the reaction mixture plus the wash after the specified reaction time.

The materials used in the following examples had the following characteristics:

Cesium formate (Alfa), triisobutyl aluminum (Alfa), ammonium benzoate (PCR "veripur" grade), aluminum acetylacetonate (Alfa), aluminum isopropoxide (Alfa), aluminum lacetate (City Chemical), aluminum oxalate (City Chemical), triphenyl aluminum (ROC/RIC), and tetraglyme (Ansul) were used without further purification. Sulfolane (Phillips) was purified as described by Arnett.[1] Cesium benzoate[2] (recryst. $H_2O$, Anal. Found: C, 32.62; H, 1.90. Calcd. for $C_7H_5O_2Cs$: C, 33.10; H, 1.98), triethanolamine aluminate[3] [nmr ($CDCL_3$): $\tau =$ 6.2 (br m,6.0 H), 7.2 (br m, 6.0 H)], and triisopropanolamine aluminate[3c,4] [mp (toluene) 187°-193° (isomer mixture ?); nmr ($CDCL_3$): $\tau =$ 5.8 (br m, 3.0 H), 7.3 (br m 6.0 H), 8.8 (br m, 6.0 H)] were prepared by use of literature procedures.

REFERENCES (1) E. N. Arnett and C. F. Douty, J. Am. Chem. Soc., 86, 409 (1964).
(2) J. H. S. Green, W. Kynaston, and A. S. Lindsey, Spectrochim. Acta, 17, 486 (1961).
(3)
   (a) Fr. Hein and P. W. Albert, Z. anorg. allgem. Chem., 269, 67 (1952);
   (b) I. N. Elbling and A. B. Finestone, Can. 665743 (1963);
   (c) W. M. Thomas, S. J. Groszos, and N. E. Day, U.S. 2985685 (1961).
(4) J. M. Icken and E. J. Jahren, U.S. 3448189 (1969).

TABLE

COMPOUNDS OF ALUMINUM AS PROMOTERS OF PROPYLENE GLYCOL FORMATION

| Examples | Salt (mmoles) | Solvent | T° C. | Al Compound (mmoles) | Propylene Glycol,g | Methanol,g | Ethylene Glycol,g | % Rh Recovered |
|---|---|---|---|---|---|---|---|---|
| 1 | $HCO_2Cs$ (0.65) | Sulfolane | 240° | — | — | 2.84 | 4.90 | 80 + 4 |
| 2 | " | " | " | triethanolamine aluminate (2.5) | 0.82 | 2.91 | 1.80 | 79 + 4 |
| 3 | " | " | " | triethanolamine aluminate (5.0) | 0.71 | 3.25 | 1.30 | 79 + 5 |
| 4 | " | " | " | triisopropanolamine aluminate (2.5) | 1.06 | 2.15 | 1.97 | 80 + 5 |
| 5 | " | " | " | triisopropanolamine aluminate (5.0) | 1.20 | 2.70 | 1.70 | 78 + 5 |
| 6 | " | " | " | triisobutyl aluminum (5.0) | 0.70 | 2.30 | 1.70 | 66 + 5 |
| 7 | — | " | 260° | triisopropanolamine aluminate (2.5) | — | 3.86 | 2.30 | 73 + 4 |
| 8 | $PhCO_2NH_4$ (0.65) | " | " | — | — | 4.53 | 4.90 | 66 + 3 |
| 9 | " | " | " | triisopropanolamine aluminate (2.5) | 1.47 | 4.50 | 2.05 | 80 + 2 |
| 10 | " | " | " | aluminum acetylacetonate (5.0) | 0.90 | 3.89 | 1.40 | 75 + 5 |
| 11 | " | " | " | aluminum isoproxide (5.0) | 0.77 | 4.30 | 1.15 | 75 + 5 |
| 12 | " | " | " | aluminum lactate (5.0) | 0.66 | 2.31 | 1.15 | 46 + 5 |
| 13 | " | " | " | aluminum oxalate (2.5) | — | 0.18 | — | 63 + 4 |
| 14 | " | " | " | triisobutylaluminum (5.0) | 0.53 | 3.25 | 2.00 | 59 + 8 |
| 15 | " | " | " | triphenylaluminum | 0.43 | 3.13 | 1.60 | 81 + 6 |

TABLE-continued

COMPOUNDS OF ALUMINUM AS PROMOTERS OF PROPYLENE GLYCOL FORMATION

| Examples | Salt (mmoles) | Solvent | T° C. | Al Compound (mmoles) | Propylene Glycol,g | Methanol,g | Ethylene Glycol,g | % Rh Recovered |
|---|---|---|---|---|---|---|---|---|
| 16 | " | " | " | triisopropanolamine aluminate (2.5) + 6.0g ethylene glycol[a] | 1.29 | 4.57 | 6.10 | 71 + 3 |
| 17 | " | " | " | triisopropanolamine aluminate (2.5) + 8.9g glycerine[b] | 2.18 | 4.91 | 3.08 | 83 + 1 |
| 18 | — | Tetraglyme | 220° | triisopropanolamine aluminate (2.5) | — | 1.40 | 2.70 | 48 + 8 |
| 19 | PhCO$_2$Cs (0.65) | " | 240° | — | — | 2.15 | 2.90 | 27 + 52 |
| 20 | " | " | " | triisopropanolamine aluminate (2.5) | 0.91 | 3.40 | 3.05 | 73 + 6 |
| 21 | " | " | " | triisobutyaluminum (2.5) | — | 0.85 | — | 13 + 45 |
| 22 | " | " | " | triphenylaluminum (2.5) | 0.07 | 1.09 | 0.22 | 8 + 51 |

Data for all runs at H$_2$/CO = 1, 8000 psig, 4 hr., 75 ml solvent, 3.0 mmoles Rh(C0)$_2$ acac.
[a]would analyze to be 5.4g in the ethylene glycol column.
[b]would analyze to be 8.0g in the glycerine column.

What is claimed is:

1. A process for producing alkane polyols in a homogeneous liquid phase mixture which comprises reacting at a temperature of from about 100° C. to about 375° C. and a pressure of from about 500 psia to about 50,000 psia hydrogen and oxides of carbon in the presence of a rhodium carbonyl complex and a compound of aluminum selected from the group consisting of aluminum carboxylates, trialkyl and triaryl aluminum compounds, aluminum alkanedionates, aluminum alkoxides, aluminum aryloxides and alkanolamine aluminates.

2. The process of claim 1 wherein the temperature is from about 210° C. to about 290° C.

3. The process of claim 1 wherein the reaction is effected in the presence of an organic solvent.

4. The process of claim 1 wherein the compound of aluminum is a trialkanolamine aluminate.

5. The process of claim 1 wherein the reaction is effected in the presence of an organic Lewis base compound.